United States Patent
Bailey

(10) Patent No.: US 11,211,236 B2
(45) Date of Patent: Dec. 28, 2021

(54) OPERATING A MASS SPECTROMETER UTILIZING A PROMOTION LIST

(71) Applicant: Thermo Finnigan LLC, San Jose, CA (US)

(72) Inventor: Derek J. Bailey, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 16/427,050

(22) Filed: May 30, 2019

(65) Prior Publication Data

US 2020/0381231 A1    Dec. 3, 2020

(51) Int. Cl.
*H01J 49/00* (2006.01)
*G01N 30/72* (2006.01)
*G01N 33/487* (2006.01)

(52) U.S. Cl.
CPC ...... *H01J 49/0036* (2013.01); *G01N 30/7233* (2013.01); *G01N 33/487* (2013.01); *H01J 49/004* (2013.01); *H01J 49/0031* (2013.01)

(58) Field of Classification Search
CPC .. H01J 49/0036; H01J 49/004; H01J 49/0031; G01N 30/7233; G01N 33/487
USPC ................. 250/281, 282, 283, 288
See application file for complete search history.

(56) References Cited

U.S. PATENT DOCUMENTS

| | | | |
|---|---|---|---|
| 7,473,892 B2 * | 1/2009 | Sano | G01N 33/6848 250/281 |
| 7,498,568 B2 | 3/2009 | Overney et al. | |
| 8,168,943 B2 | 5/2012 | Schwartz et al. | |
| 8,987,662 B2 * | 3/2015 | Satulovsky | H01J 49/0036 250/287 |
| 9,911,587 B1 * | 3/2018 | Li | H01J 49/0031 |
| 10,557,837 B2 * | 2/2020 | Kageyama | G01N 30/8675 |
| 2006/0169889 A1 * | 8/2006 | Yokosuka | H01J 49/004 250/288 |
| 2011/0288779 A1 * | 11/2011 | Satulovsky | H01J 49/0031 702/19 |
| 2012/0261568 A1 | 10/2012 | Coon et al. | |
| 2016/0254129 A1 | 9/2016 | Richardson et al. | |

FOREIGN PATENT DOCUMENTS

| | | |
|---|---|---|
| EP | 1717586 A1 | 11/2006 |
| EP | 3340275 A1 | 6/2018 |

OTHER PUBLICATIONS

Yokosuka, et al ("Information-Based-Acquisition (IBA) technique with an ion-trap/time-of-flight mass spectrometer for high-throughput and reliable protein profiling," Rapid Comm. Mass Spectrom. 2006, 20: pp. 2589-2595) (Year: 2006).*

(Continued)

*Primary Examiner* — Michael Maskell

(57) ABSTRACT

Real-time search (RTS) for mass spectrometry is described. In one aspect, a mass spectrometer can identify a candidate peptide for a product ion spectrum by searching a mass spectral database. While executing the search of the mass spectral database, a candidate peptide score representing a confidence of a match between the product ion spectrum and a theoretical mass spectrum stored in the mass spectral database is generated. A failing score can be promoted to a passing result based on attributes of the candidate peptide.

20 Claims, 6 Drawing Sheets

(56) References Cited

OTHER PUBLICATIONS

Erickson et al. "Active Instrument Engagement Combined with a Real-Time Database Search for Improved Performance of Sample Multiplexing Workflows," Journal of Proteome Research, Jan. 18, 2019, vol. 18, pp. 1299-1306.
Extended EP Search Report dated Oct. 9, 2020, for EP Patent Application No. 20167409.0.
Graumann J, et al., "A Framework for Intelligent Data Acquisition and Real-Time Database Searching for Shotgun Proteomics*," Molecular & Cellular Proteomics, 2012, vol. 13, No. 3, M111. 013185, 11 pages.
Rudomin E.L, et al., "Directed sample interrogation utilizing an accurate mass exclusion-based data-dependent acquisition strategy (AMEx)," J Proteome Res., Jun. 2009, vol. 8, No. 6, pp. 3154-3160.
Schwudke D, et al., "Shotgun Lipidomics by Tandem Mass Spectrometry under Data-Dependent Acquisition Control," Methods in Enzymology, 2007, vol. 433, pp. 175-191.
Yokosuka T, et al., "'Information-Based-Acquisition' (IBA) technique with an ion-trap/time-of-flight mass spectrometer for high-throughput and reliable protein profiling," Rapid Communications in Mass Spectrometry, 2006, vol. 20, No. 17, pp. 2589-2595.

* cited by examiner

OPERATING A MASS SPECTROMETER UTILIZING A PROMOTION LIST

TECHNICAL FIELD

This disclosure relates to apparatus and methods for mass spectrometry, and more particularly to data-dependent operation of a mass spectrometer using results of a search of a promotion list.

BACKGROUND

A current focus of biological mass spectrometry is the identification, quantification, and structural elucidation of peptides, proteins, and related molecules. In such experiments, it is often necessary or desirable to perform controlled fragmentation of certain ions (referred to as tandem or MSn mass spectrometry) to yield product ions, whose mass spectra provides information that may be highly useful to confirm identification or to derive structural details regarding analytes of interest. One commonly used method for MSn mass spectrometry is called data-dependent acquisition (DDA, alternatively referred to as information-dependent acquisition). The DDA technique utilizes data acquired in one mass analysis scan to automatically select, based on predetermined criteria, one or more ion species for mass isolation and fragmentation. For example, the mass spectrometer may be configured to perform a full MS (precursor ion) scan, and then select one or more ion species from the resulting spectra for subsequent MSn analysis scans based on criteria such as intensity, charge state, mass-to-charge ratio (m/z), inclusion/exclusion lists, or isotopic patterns. The DDA technique provides benefits of simplifying product ion spectra (by selecting only certain ion species for fragmentation, thereby avoiding the need to deconvolute complex product ion spectra including product ions produced from disparate precursor ions), and making efficient use of instrument time (by excluding from MSn analysis ions that do not meet the predetermined criteria and hence may not be of interest to the researcher).

Peptide identification is typically performed by searching the experimentally-acquired mass spectra against a mass spectral database including theoretical mass spectra calculated using known peptide amino acid or genetic sequences, or an empirical library of previously acquired and curated spectra. Historically, database searching is performed post-acquisition, i.e., after all of the analysis scans have been completed. More recently (see, e.g., Erickson et al., "Active Instrument Engagement Combined with a Real-Time Database Search for Improved Performance of Sample Multiplexing Workflows", J. Proteome Research, vol. 18, pp. 1299-1306 (2019), the disclosure of which is incorporated herein by reference), improved search algorithms and more powerful processors have enabled the implementation of real-time search (RTS) of mass spectral databases, in which an experimental mass spectra can be rapidly searched against a mass spectral database and one or more peptide ions present in the spectra can be identified (at least tentatively) within a time that is short relative to the duration of the presence of ion species within the mass spectrometer (e.g., the duration of a chromatographic elution peak). Using RTS, data-dependent acquisition can be performed based on criteria involving the identification of peptide ions in the spectra. This technique may be particularly valuable within the context of proteomics experiments where samples contain a complex mixture of peptides of interest and other molecules (e.g., matrix-derived substances, as well as highabundant species that may not be of interest), allowing the researcher to increase the instrument scan time spent on MSn analysis of biologically significant peptides.

In RTS, the peptide of the experimentally-acquired mass spectrum is identified by calculating scores for the theoretical or empirical mass spectra stored in the mass spectral database. The scores represent how similar the experimental mass spectrum is to the mass spectra in the mass spectral database. The mass spectrum with the highest score is used as a match if the highest score is above a minimum score number (which may be specified by the operator or set to a default value) to ensure a certain level of confidence of the match. Thus, the corresponding peptide of the mass spectrum with the highest score can be the peptide of the experimental mass spectrum. An additional MS scan (MS3) can then be performed for one of the product ions for further analysis if the peptide is of interest (e.g., as dictated by the analytical rules).

In conventional application of RTS, if the highest score is below the minimum score, it can be concluded that a matching peptide was not identified with sufficient confidence. Thus, an additional MS scan (MS3) can be refrained from operating on the product ions and, therefore, different precursor ions are selected or fragmented differently to form other product ions for analysis.

However, some peptides might be of interest for further analysis, but have a score slightly below the minimum score. Unfortunately, these peptides would not be further analyzed with additional MS scans. Additionally, some peptides might have a score that is well above the minimum score, but not be of interest. For example, peptides derived from keratin might not be of interest for further analysis, but be subject to additional MS scans due to the score being above the minimum score. Thus, the number of scans of the mass spectrometer dedicated to peptides of interest to the experiment is often reduced and, therefore, fewer relevant data points are collected.

SUMMARY

Figure 1:
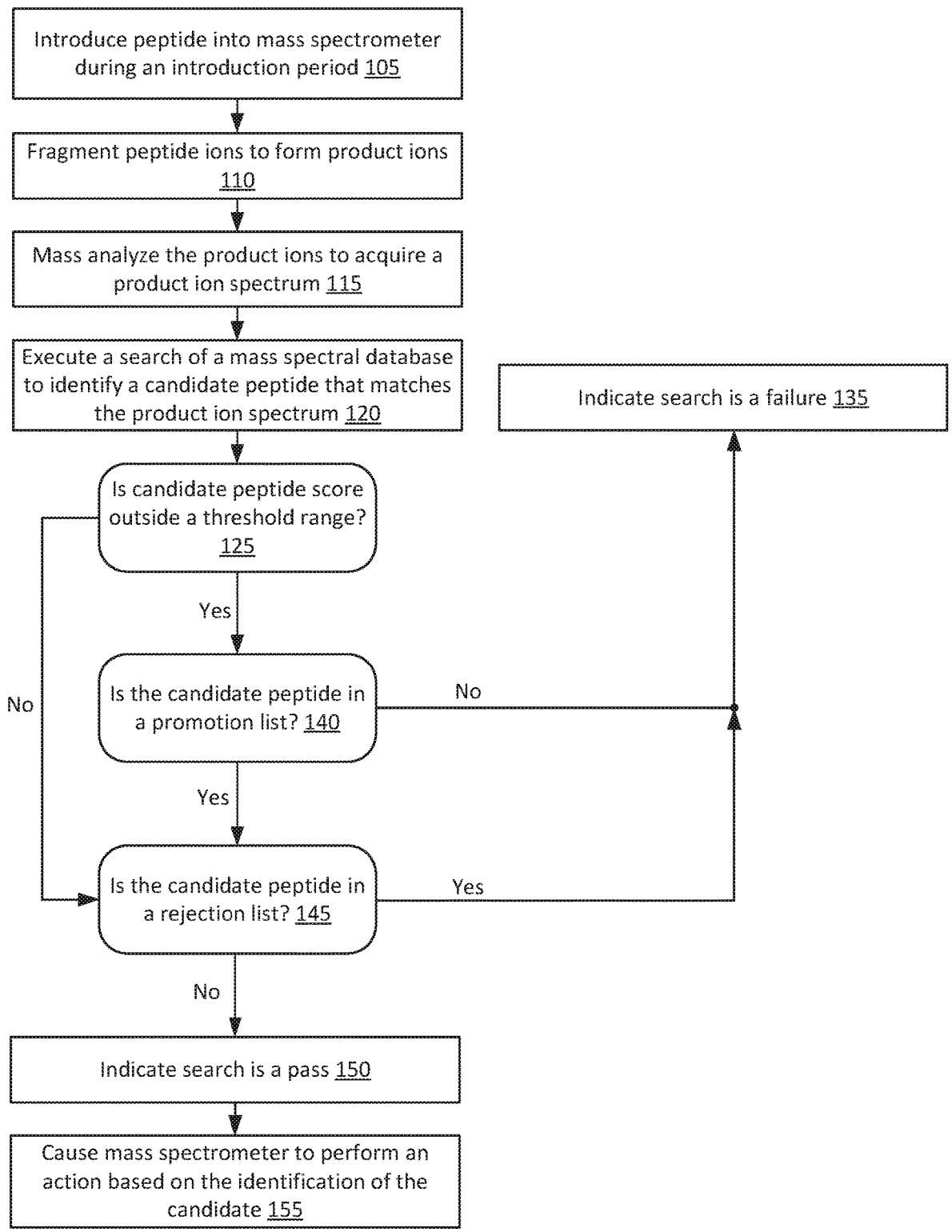
FIG. 1 illustrates an example of a block diagram for performing a real-time search (RTS) for a mass spectrometer.

One innovative aspect of the subject matter described in this disclosure includes a method of operating a mass spectrometer to analyze a biological sample. The method includes: introducing peptide ions generated from the biological sample into the mass spectrometer during an introduction period; fragmenting the peptide ions to form product ions; mass analyzing the product ions to acquire a product ion spectrum; and during the introduction period, using a programmed controller to perform: executing a search of a mass spectral database to identify a candidate peptide in the mass spectral database that matches the product ion spectrum, and the search of the mass spectral database including generating a candidate peptide score indicative of a confidence of the match for the candidate peptide, determining that the candidate peptide score is outside of a threshold score range that is representative of a confident match for the product ion spectrum, determining that the candidate peptide includes an attribute that is indicated in a promotion list representative of attributes of peptides that are of interest for the analysis of the biological sample, and upon determination that the candidate peptide includes the attribute, causing the mass spectrometer to perform an action based on the determination that the candidate peptide includes an attribute indicated in the promotion list.

In some implementations, introducing peptide ions includes ionizing a chromatographically separated component of the biological sample, the introduction period being defined by a chromatographic elution peak width of the chromatographically separated component.

In some implementations, the attributes indicated in the promotion list are defined by a user.

In some implementations, the programmed controller is to further perform: determining that the candidate peptide does not include an attribute that is indicated in a rejection list representative of attributes of peptides that are not of interest for the analysis of the biological sample, and wherein causing the mass spectrometer to perform the action is also based on the determination that the candidate peptide does not include an attribute indicated in the rejection list.

In some implementations, the programmed controller is to further perform: modify the promotion list or the rejection list based on the determination that the candidate peptide includes an attribute that is indicated in the promotion list or the determination that the candidate peptide does not include an attribute that is indicated in the rejection list.

In some implementations, the attributes of peptides indicated in the promotion list includes a protein that the candidate peptide is derived from.

In some implementations, the attributes of peptides indicated in the promotion list includes a biological system of an organism related to the candidate peptide or a protein from which the candidate peptide is derived from.

In some implementations, the action to be performed includes performing an additional stage of MSn analysis for one or more of the product ions.

Another innovative aspect of the subject matter described in this disclosure includes an apparatus for analyzing a biological sample. The apparatus includes: a separation device configured to temporally separate the biological sample into components; an ionization source configured to receive a component of the biological sample and generate peptide ions from the component during an introduction period; a fragmentation device configured to fragment the peptide ions to form product ions; a mass analyzer configured to analyze the product ions to produce a product ion spectrum; and a controller programmed with instructions for: executing a search of a mass spectral database to identify a candidate peptide in the mass spectral database that matches the product ion spectrum, and the search of the mass spectral database including generating a candidate peptide score indicative of a confidence of the match for the candidate peptide, determining that the candidate peptide score is outside of a threshold score range that is representative of a confident match for the product ion spectrum, determining that the candidate peptide includes an attribute that is indicated in a promotion list representative of attributes of peptides that are of interest for the analysis of the biological sample, and upon determination that the candidate peptide includes the attribute, causing the mass spectrometer to perform an action based on the determination that the candidate peptide includes an attribute indicated in the promotion list.

In some implementations, peptide ions includes ionizing a chromatographically separated component of the biological sample, the introduction period being defined by a chromatographic elution peak width of the chromatographically separated component.

In some implementations, the attributes indicated in the promotion list are defined by a user.

In some implementations, the controller is further programmed with instructions for: determining that the candidate peptide does not include an attribute that is indicated in a rejection list representative of attributes of peptides that are not of interest for the analysis of the biological sample, and wherein causing the mass spectrometer to perform the action is also based on the determination that the candidate peptide does not include an attribute indicated in the rejection list.

In some implementations, the controller is further programmed with instructions for: modifying the promotion list or the rejection list based on the determination that the candidate peptide includes an attribute that is indicated in the promotion list or the determination that the candidate peptide does not include an attribute that is indicated in the rejection list.

In some implementations, the attributes of peptides indicated in the promotion list includes a protein that the candidate peptide is derived from.

In some implementations, the attributes of peptides indicated in the promotion list includes a biological system of an organism related to the candidate peptide or a protein from which the candidate peptide is derived from.

In some implementations, the action to be performed includes performing an additional stage of MSn analysis for one or more of the product ions.

Another innovative aspect of the subject matter described in this disclosure includes an apparatus including: a mass analyzer configured to analyze ions to produce a mass spectrum; and a controller programmed with instructions for: executing a search of a mass spectral database to identify a candidate molecule in the mass spectral database that matches the mass spectrum, and the search of the mass spectral database including generating a candidate molecule score indicative of a confidence of the match for the candidate molecule, determining that the candidate molecule score is outside of a threshold score range that is representative of a confident match for the product ion spectrum, determining that the candidate molecule includes an attribute that is indicated in a promotion list representative of attributes of the molecule that are of interest, and upon determination that the candidate molecule includes the attribute, causing the mass spectrometer to perform an action based on the determination that the candidate molecule includes an attribute indicated in the promotion list.

In some implementations, the ions are product ions, and the action to be performed includes performing an additional stage of MSn analysis for one or more of the product ions.

In some implementations, the attributes of the molecules indicated in the promotion list includes a protein that the ion is derived from.

In some implementations, the attributes of the molecules indicated in the promotion list includes a biological system of an organism related to the candidate molecule or a larger molecule from which the candidate molecule is derived from.

DETAILED DESCRIPTION

Some of the material described in this document includes mass spectrometers and techniques for real-time searching (RTS). In one example, a mixture including peptides is introduced into a chromatography system such that different peptides in the mixture are separated and introduced into a mass spectrometer for analysis at different times. The introduction period of a chromatographically separated peptide into the mass spectrometer (i.e., the time between when the peptide begins to elute from the chromatographic column and is delivered to the mass spectrometer inlet, and when elution is completed) is determined by the chromatographic peak width and defines the time available to perform mass spectrometry (MS) operations on the peptide.

In RTS for proteomics, an experimental mass spectrum generated by the mass spectrometer is used to search a mass spectral database. A mass spectral database includes an electronically-stored collection of information that includes either or both of (i) data, such as amino acid sequences for peptides and/or proteins, that may be employed to generate theoretical mass spectra based on predetermined rules (e.g., proteolysis cleavages, fragmentation predictions, etc.), or (ii) empirically derived spectra acquired previously for identified peptides (i.e., a spectral library), though other types of information related to peptides and/or proteins can also be stored. The theoretical or empirically-derived mass spectra contained in or derived from the mass spectral database includes a list of ion m/z's and optionally the corresponding measured or predicted intensities.

A candidate peptide score representing a confidence or a likelihood of a match between the experimental mass spectrum and the theoretical or empirical mass spectra is calculated for each of the mass spectra (or, in some cases, a subset of the mass spectra satisfying predetermined criteria, such as precursor m/z range or organism/tissue type) stored in the mass spectral database. The mass spectrum with the highest candidate peptide score is then identified as the match (e.g., identify the peptide associated with the experimental mass spectrum). Using data-dependent analysis (DDA) rules, if that peptide is of interest for further analysis, then additional operations of the mass spectrometer can be performed on product ions of the peptide (e.g., MS3 operations can be performed). These operations occur during the introduction time.

As described later herein, whether the candidate peptide score is above a threshold range is determined. If the candidate peptide score is outside the threshold range, which indicates that the confidence of the match of the experimental mass spectrum with the theoretical mass spectrum is low, then a promotion list detailing information regarding peptides that are of interest for the experiment can be searched to bypass the rejection of the peptide for further MS operations due to the low candidate peptide score. This results in a "promotion" of the candidate peptide for further MS operations such as performing MS3 operations on the product ions of the peptide. Additionally, a rejection list can also be checked to determine whether further MS operations on the peptide should be refrained from being performed, resulting in a "rejection" of the peptide for further MS operations.

By using one or both of the promotion list or the rejection list, the mass spectrometer can spend more time focusing on peptides of particular biological interest. For example, a peptide candidate might have a relatively low score, but include criteria detailed in the promotion list that is of biological interest (e.g., peptides from proteins from a liver can be promoted using the promotion list even if the candidate peptide score is low). Likewise, a peptide candidate with a relatively high score can be excluded if the peptide is not of biological interest, for example, a peptide that is often seen as background contamination. This, in turn, increases the amount of useful data points for the experiment because the relatively short time duration of the introduction period of the peptide can be used for more meaningful operations.

Figure 2:
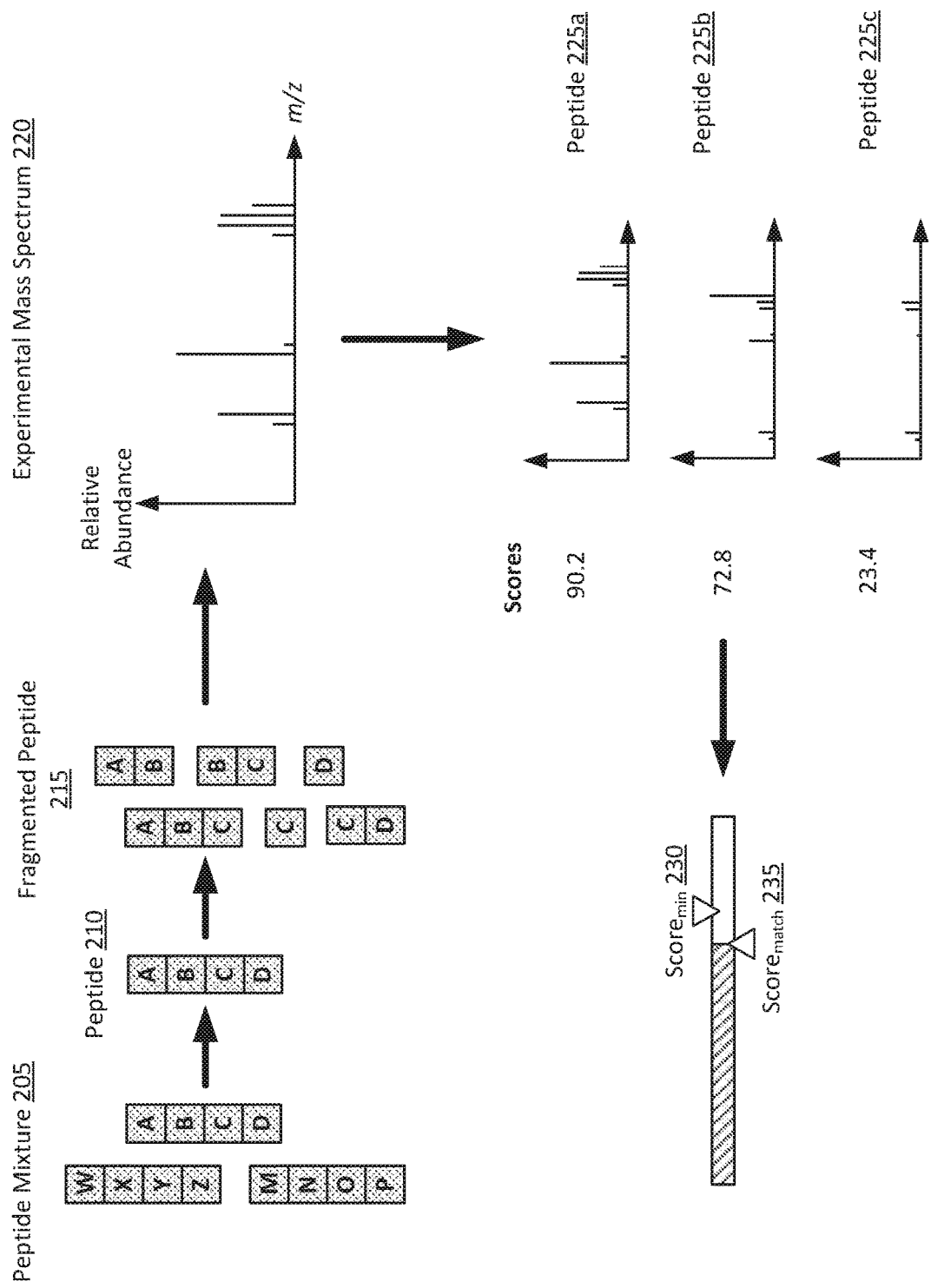
FIGS. 2 and 3 illustrate an example of performing a RTS for a mass spectrometer.
Figure 3:
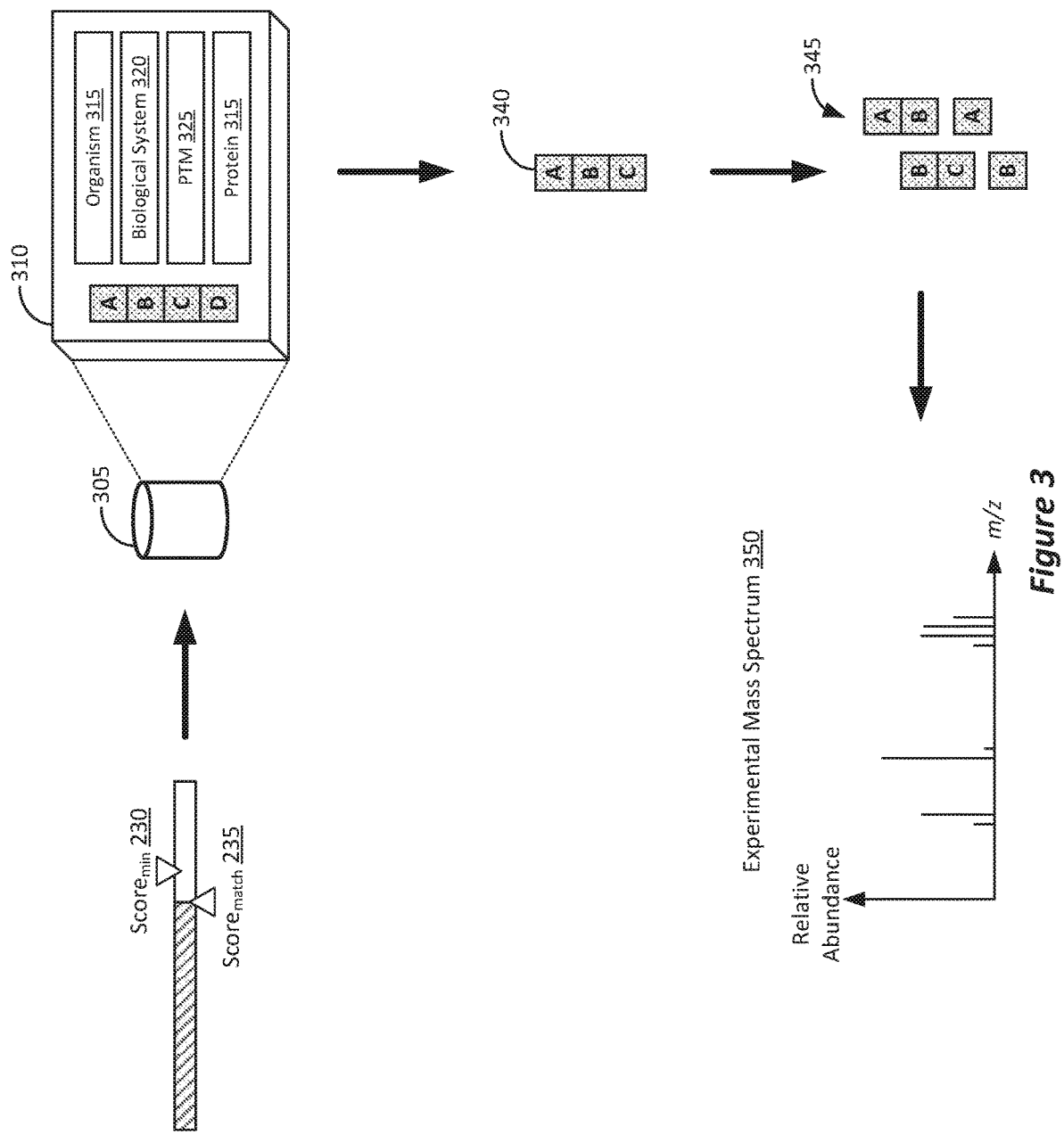

In more detail, FIG. 1 illustrates an example of a block diagram for performing a real-time search (RTS) for a mass spectrometer. FIGS. 2 and 3 illustrate an example of performing a RTS for a mass spectrometer. In FIG. 1, a peptide is separated from other peptides (and other components) in a mixture (105). Techniques to separate the peptide can include liquid chromatography (LC), gas chromatography (GC), capillary electrophoresis (CE), or other types of systems used to separate components of a mixture. In the example of proteins subject to digestion, the separate components of the mixture are peptides (e.g., portions of the protein). In FIG. 2, this is depicted as peptide mixture 205, which includes three different types of peptides including peptide 210. The peptides are separated in space, or position, within a flow path such as a chromatographic column (if using LC) such that the peptides are introduced into the mass spectrometer at different times. Thus, in FIG. 2, peptide 210 is introduced into the mass spectrometer at a separate time than other peptides in peptide mixture 205.

If using LC or GC, introducing the peptide can be performed within the introduction period, which can be defined by a chromatographic elution peak width of the chromatographic instrumentation. That is, the introduction period can be defined by the time that the concentration of the analyte (e.g., peptide) has started to separate from other components of the mixture and the time that the solute elutes.

Peptide 210 can then be ionized to form precursor ions, for example, using an ion source that removes or adds charge-carrying entities (e.g., hydrogen nuclei or electrons) to or from the peptide as the material under analysis. This results in the peptide ions having positive or negative charge. The ion source will typically be electrospray ionization (ESI), but any other suitable ionization technique including atmospheric-pressure chemical ionization (APCI) or atmospheric pressure photoionization (APPI) can be used.

Next, the precursor ions are mass selected or isolated in a first mass spectrometry scan (MS1). For example, the precursor ions of the peptide formed by the ion source are transported via ion optics to a mass selector. The mass selector may take the form, in one example, of a quadrupole mass filter in which the amplitudes of the radio-frequency (RF) and resolving direct current (DC) voltages are adjusted such that only ions within a narrow range of m/z values are transmitted. Alternatively, the mass selector may be any suitable device capable of isolating ions within a m/z window of interest, such as an analytical ion trap or time-of-flight (TOF) mass analyzer. In other words, some of the precursor ion species are mass isolated.

Returning to FIG. 1, the peptide ions (as precursor ions) are then fragmented to form product ions (110). For example, a fragmentation cell receives the precursor ions from the mass selector and fragments, or breaks up, the precursor ions into smaller product ions. In FIG. 2, this is depicted as fragmented peptide 215, which includes peptides that are smaller portions of peptide 210.

Fragmentation is often performed on larger molecules, such as peptides, to allow for more detailed understanding of the structural composition of the molecule. The fragmentation cell can be implemented using many different types of disassociation techniques including collision-induced disassociation (CID), surface-induced dissociation (SID), electron-capture dissociation (ECD), electron-transfer dissociation (ETD), negative electron-transfer dissociation (NETD), electron-detachment dissociation (EDD), photodissociation, higher-energy C-trap dissociation (HCD), etc.

Next, in FIG. 1, the product ions are mass analyzed to acquire a product ion spectrum (115). For example, in FIG. 2, the product ions formed by the fragmentation cell are provided to a mass analyzer, mass separated, and then provided to a detector. The mass analyzer can be any suitable device for separating ions according to their mass-to-charge ratios, including (without limitation) an orbital electrostatic trap, analytical quadrupole ion trap, Fourier Transform-Ion Cyclotron Resonance (FT-ICR) analyzer, TOF mass analyzer, or a quadrupole mass filter.

The detector can detect induced charge or current produced when the product ions provided by the mass analyzer pass by or hit a surface of the detector. Thus, the detector generates signals representative of the m/z of the product ions. These signals are then provided to a programmed controller circuit to generate a mass spectrum using the detected signals. In FIG. 2, experimental mass spectrum 220 depicts the product ion mass spectrum of fragmented peptide 215 that is determined by the programmed controller circuit. The y-axis represents the relative abundance of a product ion and the x-axis represents the m/z of a product ion.

Returning to the block diagram of FIG. 1, a search of a mass spectral database is then executed to identify a candidate peptide that matches the product ion spectrum (120). The search to identify the candidate peptide includes searching a mass spectral database storing data related to candidate mass spectra (e.g., theoretical mass spectra or empirically determined mass spectra, as previously discussed).

By comparing experimental mass spectrum 220 with the candidate mass spectra of candidate peptides, a candidate peptide score can be generated for each (or a subset) of the mass spectra of the mass spectral database. For example, as depicted in FIG. 2, peptide 225a has a score of 90.2, peptide 225b has a score of 72.8, and peptide 225c has a score of 23.4. The candidate peptide score represents a confidence, or likelihood, of a match between experimental mass spectrum 220 and the candidate mass spectrum. A higher score indicates a higher confidence of the match. In the example of FIG. 2, because the mass spectrum of peptide 225a is associated with the highest score, peptide 225a is a possible match for peptide 210 (i.e., peptide 210 can be identified as peptide 225a in view of the similarities of their corresponding mass spectra).

The information providing the data for the candidate mass spectra can be stored in a database. As previously discussed, the information stored in the database can include amino acid sequences or empirically determined or derived mass spectra. Additionally, the identification of the peptide candidate can include matching the m/z positions on the x-axis and relative abundance on the y-axis of experimental mass spectrum 220 with the stored information. However, other applications might use less or more information. For example, for faster searching, only the m/z positions (or a peak list) on the x-axis of experimental mass spectrum 220 are used to identify a candidate peptide. Some examples of algorithms that can be used for protein identification include SEQUEST, Mascot, MOWSE, COMET, etc.

Returning to FIG. 1, the candidate peptide score can be determined whether it is outside of a threshold range (125). For example, in FIG. 2, $Score_{match}$ 235 (i.e., the candidate peptide score) for peptide 225a is 90.2. $Score_{min}$ 230 represents the minimum score for a candidate peptide score to have a minimum confidence as to the identification of the match and possibly perform additional MS operations (e.g., MS3) on a product ion. Thus, the range from $Score_{min}$ 230 to the maximum score is a threshold range for $Score_{match}$ 235 to be considered a confident match, or high likelihood of a match. If $Score_{match}$ 235 is outside of the threshold range (e.g., by being below $Score_{min}$ 230), then the identification of peptide 225a as the match is a lower confidence and, therefore, perhaps further MS operations such as MS3 should not be performed. Though MS3 operations are described in the examples herein, any MSn operation can be performed (e.g., MS4, MS5, etc. wherein n is a positive integer) for subsequent stages of mass spectrometry.

In FIG. 1, if the candidate peptide score is within the threshold range (e.g., 90 to 100), then a rejection list can be searched to determine if the candidate peptide is not of interest (145), as will be discussed later herein. However, if the candidate peptide score is outside of the threshold range, then a promotion list can be checked to determine if the candidate peptide includes attributes listed therein (140). For example, as depicted in FIG. 3, promotion list 305 identifies specific attributes, or characteristics, of peptides that are of interest despite having a low candidate peptide score. If the candidate peptide is mentioned in promotion list 305 or includes attributes mentioned in promotion list 305, then additional MS operations might be performed on the product ions despite the low score.

Promotion list 305 can detail attributes such as specific peptides that can be promoted and, in some implementations, also indicate a range for the candidate peptide score to be promoted. For example, one peptide can be promoted if the candidate peptide score is at least 70.0, and another peptide can be promoted if the candidate peptide score is at least 60.0. Thus, different peptides can be assigned different $Score_{min}$ 230 (or threshold ranges) in terms of the confidence to be promoted.

Additionally, promotion list 305 can also detail a variety of other characteristics or attributes of the candidate peptide that should be present to be promoted including organism 315, biological system 320, protein 315, and post-translational modifications (PTM) 325. For example, the protein that the peptide is derived from (e.g., via digestion) can be an attribute of a candidate peptide that, if identified, can result in the promotion of the candidate peptide. Other attributes include a type of organism (e.g., organism classes such as mammal, vertebrates or invertebrates, species, etc.), biological system that the peptide is associated with (e.g., an organ such as a liver, or an organ system such as the digestive or circulatory systems), or any post-translational modifications of the peptide or protein.

The attributes indicated in promotion list 305 can be defined by a user, for example, using a software program with a graphical user interface (GUI) to define the attributes. In another example, the user can define a list of keywords indicating the attributes. These keywords can then be searched to determine whether the candidate peptide includes an attribute that is within promotion list 305.

If the candidate peptide does not include an attribute listed in the promotion list, then the search to identify the candidate peptide can be indicated as a failure (135). This results in storing data in a memory device indicating that the search for a candidate peptide for experimental mass spectrum 220 was a failure. Because the search is a failure, MS3 operations can be refrained from being performed on the product ions.

However, in FIG. 1, if the candidate peptide includes an attribute listed in the promotion list, then it can be determined whether the candidate peptide includes an attribute listed in the rejection list (145). The rejection list can include the same or similar types of attributes as the promotion list, but include different content or data values (e.g., the promotion list can include mouse as an organism, and the rejection list can include cat as an organism). Thus, the content in the rejection list can be mutually exclusive from the content in the promotion list. If the candidate peptide includes an attribute in the rejection list, then the search is indicated as a failure (135).

If the candidate peptide includes an attribute in the promotion list and does not include an attribute in the rejection list, then the search is indicated as a pass (150), which also results in the mass spectrometer to perform an action based on the identification of the candidate peptide (155). For example, as depicted in FIG. 3, an MS3 operation can be performed on product ion 340 by fragmenting 345 into smaller ions and mass analyzed to acquire a new experimental mass spectrum 350, which is a new product ion spectrum for product ion 340.

The example of FIG. 1 includes the rejection list checked after checking the promotion list. However, the sequence of checking the rejection list and the promotion list can change, for example, the rejection list can be checked first followed by the promotion list. Additionally, only one of the promotion list or the rejection list might be used rather than both. For example, a candidate peptide can be promoted using a promotion list without any consideration of a rejection list. As another example, a candidate peptide can be rejected using a rejection list without any consideration of a promotion list.

Figure 4:
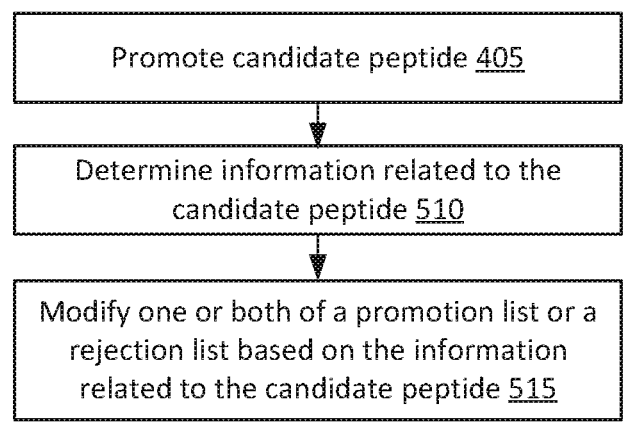
FIG. 4 illustrates an example of a block diagram for modifying a promotion list or a rejection list of a RTS.

The promotion list or the rejection list can also be modified in view of the search results. FIG. 4 illustrates an example of a block diagram for modifying a promotion list or a rejection list of a RTS. In FIG. 4, a candidate peptide is promoted (405). For example, a candidate peptide might have a candidate peptide score outside of the threshold range, but have an attribute listed in the promotion list. Next, information related to the candidate peptide is determined (410). For example, the attribute such as the protein that the peptide is from can be determined. Next, the promotion list or the rejection list is modified based on the information related to the candidate peptide (415). For example, other peptides that are digested from the same protein can be added to the promotion list. This can allow for other peptides that might be expected to be found to be identified for further analysis, which results in more data points for the mass spectrometer analysis. In another implementation, the other peptides that are digested from the same protein can be added to the rejection list. This can allow for more of the throughput of the mass spectrometer to be dedicated towards the analysis of other proteins.

As previously discussed, the candidate peptide score is evaluated in view of a threshold range. For example, in FIG. 2, $Score_{min}$ 230 is the minimum score of the threshold range that candidate peptide score should be within to provide a confident match. In some implementations, if too many searches have failed or if a consecutive number of searches have failed (e.g., ten searches in a row during the same introduction period, twenty searches in a row have failed, etc.) then the threshold range can be modified, for example, increased in range to allow for candidate peptide scores during the same introduction period or subsequent introduction periods to pass. That is, candidate peptide scores that would previously be below $Score_{min}$ 230 can then be at or above $Score_{min}$ 230 as the value of $Score_{min}$ 230 is lowered.

Figure 5:
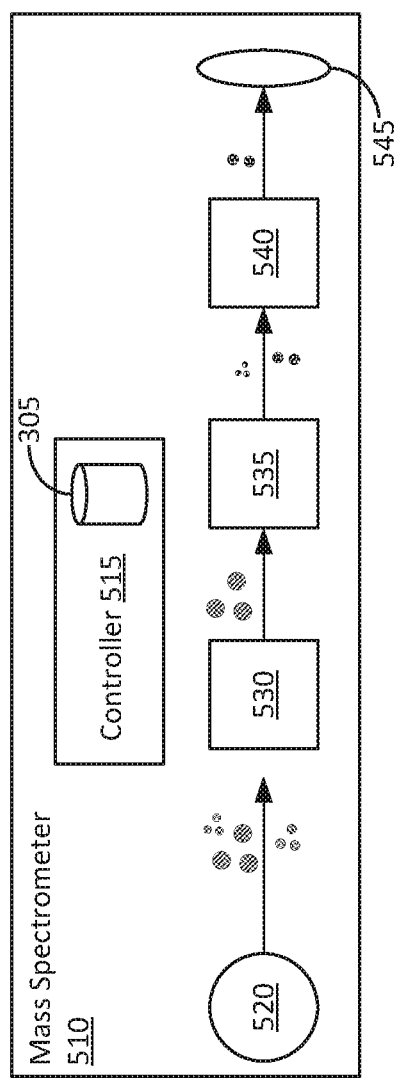
FIG. 5 illustrates an example of a mass spectrometer.

FIG. 5 illustrates an example of a mass spectrometer. In FIG. 5, mass spectrometer 510 includes ion source 520, mass selector 530, fragmentation source 535, and mass analyzer 540, detector 545, and controller circuit 515. Controller circuit 515 includes or has access to memory storing promotion list 305 (as well as a rejection list, if applicable). Controller circuit 515 also stores any DDA rules to be applied, as well as includes instructions for controlling or instructing the other components of mass spectrometer 510 to perform an action.

As previously discussed, ion source 520 receives a peptide from a separation device such as a LC system and ionizes the received peptide to form precursor ions. Mass analyzer 530 mass selects the precursor ions based on their m/z. The mass selected precursor ions are then provided to fragmentation 535 for fragmentation to form product ions. The product ions are then provided to mass analyzer 540 before being provided to detector 545. Detector 545 generates signals representative of m/z, which is interpreted by controller 515 to generate or determine information that can be used to generate a mass spectrum.

As previously discussed, in RTS, the searching is performed while the peptide is present and available for experimentation within the mass spectrometer during the introduction time. The introduction time is often relatively short, varying from the tens of seconds to several minutes. Thus, after the ionization of the peptide by the ion source during the introduction time, the peptide ions are available for mass analysis and, therefore, the experimental mass spectrum can be generated and an MS3 scan can be performed by matching the experimental mass spectrum with the mass spectrum of a candidate peptide. Thus, RTS can be performed relatively quickly such that many experimental mass spectra are determined and many decisions are made regarding whether to perform MS3, and to perform MS3, while the peptide is available.

Many of the examples describe implementations with liquid chromatography-tandem mass spectrometry (LC-MS/MS) for the identification of peptides. However, other types of mixture separation can be used including gas chromatography (GC) or capillary electrophoresis (CE).

The examples describe techniques for the RTS for a candidate peptide, however, other biomolecules can be identified and the mass spectrometer can perform a specific action upon the identification. For example, in addition to proteins and their peptides, other types of biomolecules that can be used with the techniques include lipids, nucleic acids, metabolites, oligosaccharides, polysaccharides, and the like. Moreover, other large molecules other than biomolecules can be identified, in addition to small molecules. Thus, the experimental mass spectrum can be generated for many different types of molecules, the database can store information related to possible candidates, and the RTS can be performed to identify a candidate.

The tandem mass spectrometers described in the examples can be triple quadrupole mass spectrometers (QqQ), quadrupole time-of-flight mass spectrometers (QqTOF), or other types of mass spectrometers. Additionally, while the examples describe tandem mass spectrometry in space, tandem mass spectrometry in time can also be used with the techniques described herein. In a tandem mass spectrometer in time, a single mass analyzer can be used. Moreover, more than two mass analyzers can be disposed within the mass analyzer.

The databases described in the examples are stored locally with the controller system of the mass spectrometer. However, cloud-based implementations can also be used in which the databases are stored on a remote server that is accessible by the controller. Additionally, hybrid approaches can be implemented with the RTS techniques. For example, a smaller database stored in the system of the mass spectrometer can be searched in parallel with a larger database stored in a remote server. A hybrid approach can allow for a smaller dataset that includes higher likelihood candidate peptides to be identified relatively quickly. If the peptide under analysis is not identified with the local database, the remote database can search a larger dataset to attempt to identify a candidate peptide.

Figure 6:
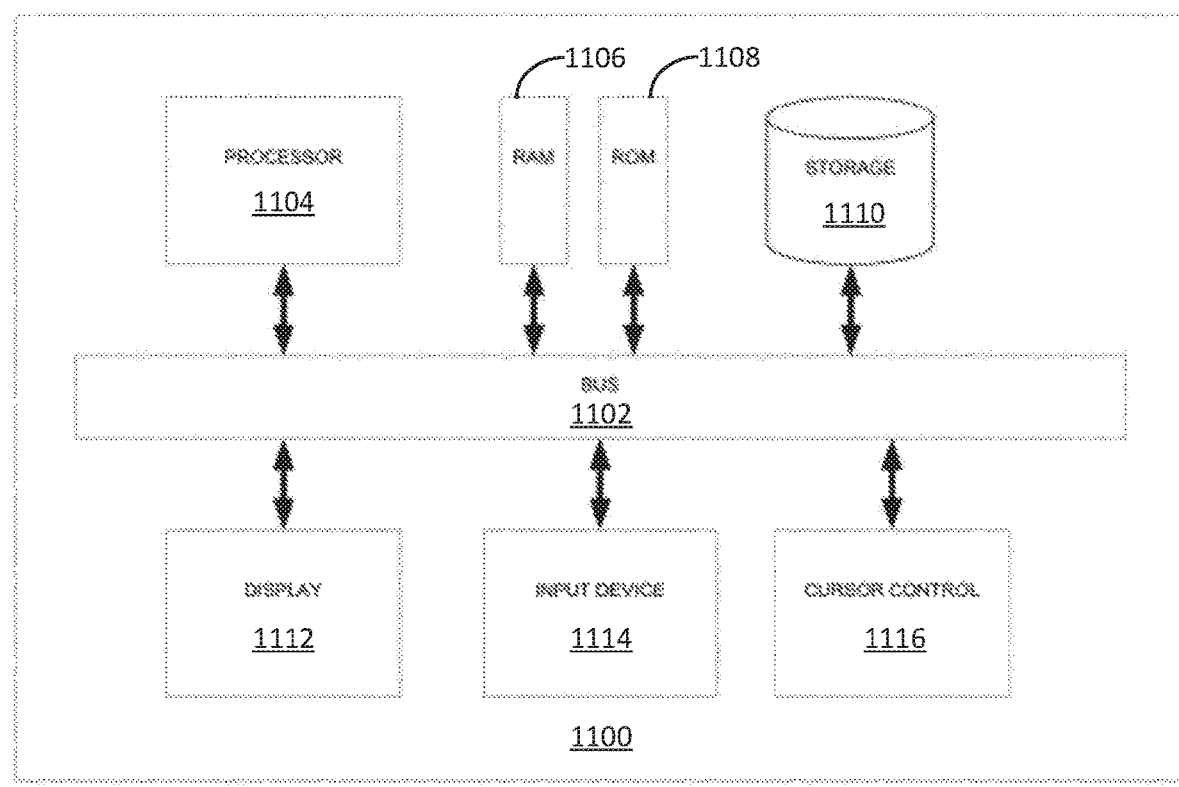
FIG. 6 illustrates an example of an electronic device which may be used to implement some of the implementations.

FIG. 6 illustrates an example of an electronic device which may be used to implement some of the implementations. The electronic device of FIG. 6 can store or use a computer program product including one or more non-transitory computer-readable media having computer programs instructed stored therein, the computer program instructions being configured such that, when executed by one or more computing devices, the computer program instructions cause the one or more computing devices to: cause introduction of peptide ions generated from the biological sample into the mass spectrometer during an introduction period; cause fragmentation of the peptide ions to form product ions; cause mass analysis of the product ions to acquire a product ion spectrum; and during the introduction period, using a programmed controller to perform: executing a search of a mass spectral database to identify a candidate peptide in the mass spectral database that matches the product ion spectrum, and the search of the mass spectral database including generating a candidate peptide score indicative of a confidence of the match for the candidate peptide, determining that the candidate peptide score is outside of a threshold score range that is representative of a confident match for the product ion spectrum, determining that the candidate peptide includes an attribute that is indicated in a promotion list representative of attributes of peptides that are of interest for the analysis of the biological sample, and upon determination that the candidate peptide includes the attribute, causing the mass spectrometer to perform an action based on the determination that the candidate peptide includes an attribute indicated in the promotion list.

In FIG. 6, computer system 1100 can implement any of the methods or techniques described herein. For example, computer system 1100 can implement controller 515 in FIG. 5. Thus, the operation of components of the associated mass spectrometer may be adjusted in accordance with calculations or determinations made by computer system 1100. In various embodiments, computer system 1100 can include a bus 1102 or other communication mechanism for communicating information, and a processor 1104 coupled with bus 1102 for processing information. In various embodiments, computer system 1100 can also include a memory 1106, which can be a random access memory (RAM) or other dynamic storage device, coupled to bus 1102, and instructions to be executed by processor 1104. Memory 1106 also can be used for storing temporary variables or other intermediate information during execution of instructions to be executed by processor 1104. In various embodiments, computer system 1100 can further include a read only memory (ROM) 1108 or other static storage device coupled to bus 1102 for storing static information and instructions for processor 1104. A storage device 1110, such as a magnetic disk or optical disk, can be provided and coupled to bus 1102 for storing information and instructions.

In various embodiments, computer system 1100 can be coupled via bus 1102 to a display 1112, such as a cathode ray tube (CRT) or liquid crystal display (LCD), for displaying information to a computer user. An input device 1114, including alphanumeric and other keys, can be coupled to bus 1102 for communicating information and command selections to processor 1104. Another type of user input device is a cursor control 1116, such as a mouse, a trackball or cursor direction keys for communicating direction information and command selections to processor 1104 and for controlling cursor movement on display 1112. This input device typically has two degrees of freedom in two axes, a first axis (i.e., x) and a second axis (i.e., y), that allows the device to specify positions in a plane.

A computer system 1100 can perform the techniques described herein. Consistent with certain implementations, results can be provided by computer system 1100 in response to processor 1104 executing one or more sequences of one or more instructions contained in memory 1106. Such instructions can be read into memory 1106 from another computer-readable medium, such as storage device 1110. Execution of the sequences of instructions contained in memory 1106 can cause processor 1104 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations described herein are not limited to any specific combination of hardware circuitry and software.

The term "computer-readable medium" as used herein refers to any media that participates in providing instructions to processor 1104 for execution. Such a medium can take many forms, including but not limited to, non-volatile media, volatile media, and transmission media. Examples of non-volatile media can include, but are not limited to, optical or magnetic disks, such as storage device 1110. Examples of volatile media can include, but are not limited to, dynamic memory, such as memory 1106. Examples of transmission media can include, but are not limited to, coaxial cables, copper wire, and fiber optics, including the wires that comprise bus 1102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the techniques are described in conjunction with various implementations or embodiments, it is not intended that the techniques be limited to such embodiments. On the contrary, the techniques encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

I claim:

1. A method of operating a mass spectrometer to analyze a biological sample, comprising:
    introducing peptide ions generated from the biological sample into the mass spectrometer during an introduction period;
    fragmenting the peptide ions to form product ions;
    mass analyzing the product ions to acquire a product ion spectrum; and
    during the introduction period, using a programmed controller to perform:
        executing a search of a mass spectral database to identify a candidate peptide in the mass spectral database that matches the product ion spectrum, and the search of the mass spectral database including generating a candidate peptide score indicative of a confidence of the match for the candidate peptide,
        determining that the candidate peptide score is outside of a threshold score range that is representative of a confident match for the product ion spectrum,
        determining that the candidate peptide includes an attribute that is indicated in a promotion list representative of attributes of peptides that are of interest for the analysis of the biological sample,
        modifying the promotion list based on the determination of the candidate peptide including the attribute, and
        upon determination that the candidate peptide includes the attribute, causing the mass spectrometer to perform an action based on the determination that the candidate peptide includes an attribute indicated in the promotion list, the action including fragmenting the product ions to form fragmented product ions and acquiring a second product ion spectrum indicative of the fragmented product ions.

2. The method of claim 1, wherein introducing peptide ions includes ionizing a chromatographically separated component of the biological sample, the introduction period being defined by a chromatographic elution peak width of the chromatographically separated component.

3. The method of claim 1, wherein the attributes indicated in the promotion list are defined by a user.

4. The method of claim 1, wherein the programmed controller is to further perform:
    determining that the candidate peptide does not include an attribute that is indicated in a rejection list representative of attributes of peptides that are not of interest for the analysis of the biological sample, and wherein causing the mass spectrometer to perform the action is also based on the determination that the candidate peptide does not include an attribute indicated in the rejection list.

5. The method of claim 4, wherein the programmed controller is to further perform:
    modify the promotion list or the rejection list based on the determination that the candidate peptide includes an attribute that is indicated in the promotion list or the determination that the candidate peptide does not include an attribute that is indicated in the rejection list.

6. The method of claim 1, wherein the attributes of peptides indicated in the promotion list includes a protein that the candidate peptide is derived from.

7. The method of claim 1, wherein the attributes of peptides indicated in the promotion list includes a biological system of an organism related to the candidate peptide or a protein from which the candidate peptide is derived from.

8. The method of claim 1, wherein the action to be performed includes performing an additional stage of MSn analysis for one or more of the product ions.

9. An apparatus for analyzing a biological sample, comprising:
- a separation device configured to temporally separate the biological sample into components;
- an ionization source configured to receive a component of the biological sample and generate peptide ions from the component during an introduction period;
- a fragmentation device configured to fragment the peptide ions to form product ions;
- a mass analyzer configured to analyze the product ions to produce a product ion spectrum; and
- a controller programmed with instructions for:
  - executing a search of a mass spectral database to identify a candidate peptide in the mass spectral database that matches the product ion spectrum, and the search of the mass spectral database including generating a candidate peptide score indicative of a confidence of the match for the candidate peptide,
  - determining that the candidate peptide score is outside of a threshold score range that is representative of a confident match for the product ion spectrum,
  - determining that the candidate peptide includes an attribute that is indicated in a promotion list representative of attributes of peptides that are of interest for the analysis of the biological sample,
  - modifying the promotion list based on the determination of the candidate peptide including the attribute, and
  - upon determination that the candidate peptide includes the attribute, causing the mass spectrometer to perform an action based on the determination that the candidate peptide includes an attribute indicated in the promotion list, the action including fragmenting the product ions to form fragmented product ions and acquiring a second product ion spectrum indicative of the fragmented product ions.

10. The apparatus of claim 9, wherein introducing peptide ions includes ionizing a chromatographically separated component of the biological sample, the introduction period being defined by a chromatographic elution peak width of the chromatographically separated component.

11. The apparatus of claim 9, wherein the attributes indicated in the promotion list are defined by a user.

12. The apparatus of claim 9, wherein the controller is further programmed with instructions for:
- determining that the candidate peptide does not include an attribute that is indicated in a rejection list representative of attributes of peptides that are not of interest for the analysis of the biological sample, and wherein causing the mass spectrometer to perform the action is also based on the determination that the candidate peptide does not include an attribute indicated in the rejection list.

13. The apparatus of claim 12, wherein the controller is further programmed with instructions for:
- modifying the promotion list or the rejection list based on the determination that the candidate peptide includes an attribute that is indicated in the promotion list or the determination that the candidate peptide does not include an attribute that is indicated in the rejection list.

14. The apparatus of claim 9, wherein the attributes of peptides indicated in the promotion list includes a protein that the candidate peptide is derived from.

15. The apparatus of claim 9, wherein the attributes of peptides indicated in the promotion list includes a biological system of an organism related to the candidate peptide or a protein from which the candidate peptide is derived from.

16. The apparatus of claim 9, wherein the action to be performed includes performing an additional stage of MSn analysis for one or more of the product ions.

17. An apparatus, comprising:
- a mass analyzer configured to analyze ions to produce a mass spectrum; and
- a controller programmed with instructions for:
  - executing a search of a mass spectral database to identify a candidate molecule in the mass spectral database that matches the mass spectrum, and the search of the mass spectral database including generating a candidate molecule score indicative of a confidence of the match for the candidate molecule,
  - determining that the candidate molecule score is outside of a threshold score range that is representative of a confident match for the product ion spectrum,
  - determining that the candidate molecule includes an attribute that is indicated in a promotion list representative of attributes of the molecule that are of interest,
  - modifying the promotion list based on the determination of the candidate peptide including the attribute, and
  - upon determination that the candidate molecule includes the attribute, causing the mass spectrometer to perform an action based on the determination that the candidate molecule includes an attribute indicated in the promotion list, the action being fragmenting the candidate molecule to form fragmented product ions and acquiring a second product ion spectrum indicative of the fragmented product ions.

18. The apparatus of claim 17, wherein the ions are product ions, and the action to be performed includes performing an additional stage of MSn analysis for one or more of the product ions.

19. The apparatus of claim 17, wherein the attributes of the molecules indicated in the promotion list includes a protein that the ion is derived from.

20. The apparatus of claim 17, wherein the attributes of the molecules indicated in the promotion list includes a biological system of an organism related to the candidate molecule or a larger molecule from which the candidate molecule is derived from.

* * * * *